(12) United States Patent
Hsieh et al.

(10) Patent No.: US 7,820,070 B2
(45) Date of Patent: Oct. 26, 2010

(54) PHOTOSENSITIVE MONOMER, LIQUID CRYSTAL MATERIAL HAVING THE SAME, LIQUID CRYSTAL PANEL AND METHOD FOR MANUFACTURING THEREOF BY INCORPORATING THE SAME, AND ELECTRO-OPTICAL DEVICE AND METHOD FOR MANUFACTURING THEREOF BY INCORPORATING THE SAME

(75) Inventors: Chung-Ching Hsieh, Hsin-Chu (TW); Shih-Feng Hsu, Hsin-Chu (TW); Te-Sheng Chen, Hsin-Chu (TW); Chao-Cheng Lin, Hsin-Chu (TW); Chia-Hsuan Pai, Hsin-Chu (TW)

(73) Assignee: Au Optronics Corp., Hsin-Chu (TW)

( * ) Notice: Subject to any disclaimer, the term of this patent is extended or adjusted under 35 U.S.C. 154(b) by 225 days.

(21) Appl. No.: 11/892,078

(22) Filed: Aug. 20, 2007

(65) Prior Publication Data
US 2008/0179565 A1 Jul. 31, 2008

(30) Foreign Application Priority Data
Jan. 31, 2007 (TW) .............................. 96103572 A (51) Int. Cl.
C09K 19/00 (2006.01)
C09K 19/06 (2006.01)
C09K 19/52 (2006.01)

(52) U.S. Cl. .............................. 252/299.01; 252/299.6; 252/299.61; 252/299.62; 252/299.63; 427/488; 548/524; 560/76; 430/20; 428/1.1

(58) Field of Classification Search ................. 427/488; 548/524; 560/76; 252/299.01, 299.1, 299.6–299.63; 428/1.1; 430/20
See application file for complete search history.

(56) References Cited

U.S. PATENT DOCUMENTS 6,861,107 B2 3/2005 Klasen-Memmer et al.

| | | |
|---|---|---|
| 2003/0160210 A1 | 8/2003 | Bremer et al. |
| 2004/0011996 A1 | 1/2004 | Klasen-Memmer et al. |
| 2005/0116200 A1 | 6/2005 | Nakanishi et al. |
| 2005/0136196 A1 | 6/2005 | Kataoka |
| 2005/0264737 A1 | 12/2005 | Kataoka et al. |
| 2006/0202162 A1 | 9/2006 | Lin et al. |
| 2007/0014934 A1 * | 1/2007 | Goulding et al. ............. 428/1.1 |

FOREIGN PATENT DOCUMENTS

CN 1475547 A 2/2004

* cited by examiner

*Primary Examiner*—Geraldina Visconti
(74) *Attorney, Agent, or Firm*—Rabin & Berdo, P.C.

(57) ABSTRACT

A photosensitive monomer of formula.

$$\left[ \begin{array}{c} L_1 \\ R_1 \\ R_2 \\ L_2 \end{array} \begin{array}{c} L_3 \\ \\ L_4 \end{array} \begin{array}{c} L_5 \\ R_3 \\ R_4 \\ L_6 \end{array} \right]_n$$

"$L_1$", "$L_2$", "$L_3$", "$L_4$", "$L_5$", "$L_6$" are selected from hydrogen, fluorine, chlorine, cyano, alkyl, alkylcarbonyl, alkoxycarbonyl, and alkylcarbonyloxy having 1 to 7 carbon atoms, in which one or more hydrogen atoms may be substituted by fluorine or chlorine.

"$R_1$", "$R_2$", "$R_3$" and "$R_4$" are selected from hydrogen, fluorine, chlorine, cyano, thiocyanato, pentafluoro sulfanyl, nitrite, straight-chained alkyl/branched alkyl, and a "Z-Sp-P" group. At least one of "$R_1$", "$R_2$", "$R_3$" and "$R_4$" is "Z-Sp-P" group. "Z" is selected from oxygen, sulfur, methyoxy, carbonyl, caroboxyl, carbamoyl, methylthio, ethenylcarbonyl, carbonylethenyl, and a single bond. "Sp" is selected from straight-chained alkyl or branched alkyl and a single bond. "P" comprises a polymerizable group.

22 Claims, 2 Drawing Sheets

PHOTOSENSITIVE MONOMER, LIQUID CRYSTAL MATERIAL HAVING THE SAME, LIQUID CRYSTAL PANEL AND METHOD FOR MANUFACTURING THEREOF BY INCORPORATING THE SAME, AND ELECTRO-OPTICAL DEVICE AND METHOD FOR MANUFACTURING THEREOF BY INCORPORATING THE SAME

This application claims the benefit of Taiwan Application No. 96103572, filed Jan. 31, 2007, the contents of which are herein incorporated by reference in its entirety.

BACKGROUND OF THE INVENTION

1. Field of the Invention

The present invention relates in general to an electro-optical device and a method for manufacturing the same, and more particularly to an electro-optical device using polymer-stabilizing alignment (PSA) technology and a method for manufacturing the same.

2. Description of the Related Art

Recently, polymer-stabilizing alignment (PSA) technology has been developed in the field of the liquid crystal panel by adding photosensitive monomers into the liquid crystal layer. After the photosensitive monomers are arranged, ultra-violet is irradiated on the photosensitive monomers so that the photosensitive monomers are polymerized into polymers with uniform orientation for guiding the liquid crystal molecules.

However, the polymers polymerized by the conventional photosensitive monomers can not regulate the alignment of the liquid crystal molecules effectively. When voltage is applied, it takes very long time to rotate all the liquid crystal molecules to a predetermined tilt angle, as a result of deteriorated quality of the liquid crystal panel.

SUMMARY OF THE INVENTION

The present invention provides a photosensitive monomer, whose hard core is an in-plane structure. When the photosensitive monomer is applied to a method for manufacturing a liquid crystal panel, the polymer polymerized by the photosensitive monomers increases the capability of regulating the alignment of the liquid crystal molecules.

According to a first aspect of present invention, a photosensitive monomer is provided. The photosensitive monomer of formula:

n = 1~2

"$L_1$", "$L_2$", "$L_3$", "$L_4$", "$L_5$", "$L_6$" are selected from hydrogen, fluorine, chlorine, cyano, alkyl, alkylcarbonyl, alkoxycarbonyl, and alkylcarbonyloxy. The alkylcarbonyloxy has 1 to 7 carbon atoms, in which one or more hydrogen atoms may be substituted by fluorine or chlorine. $R_1$", "$R_2$", "$R_3$", and "$R_4$" are selected from hydrogen, fluorine, chlorine, cyano, thiocyanato, pentafluoro sulfanyl, nitrite, straight-chained alkyl/branched alkyl, and a "Z-Sp-P" group. The straight-chained alkyl/branched alkyl has 1 to 12 carbon atoms, and one or two non-adjacent —$CH_2$ groups may be replaced by oxygen, sulfur, vinylene, carbonyl, caroboxyl, carbothio, or alkyne. At least one of "$R_1$", "$R_2$", "$R_3$", and "$R_4$" is "Z-Sp-P" group. "Z" is selected from oxygen, sulfur, methyoxy, carbonyl, caroboxyl, carbamoyl, methylthio, ethenylcarbonyl, carbonylethenyl, and a single bond. "Sp" is selected from straight-chained alkyl or branched alkyl, and a single bond. The straight-chained alkyl or branched alkyl has 1 to 8 carbon atoms, and one or two non-adjacent —$CH_2$ groups may be replaced by oxygen or sulfur. "P" is a polymerizable group.

According to a second aspect of the present invention, a liquid crystal material including liquid crystal molecules and the above-described photosensitive monomer.

According to a third aspect of the present invention, a liquid crystal panel including above-described liquid crystal material. The photosensitive monomers are polymerized into a polymer film to be functioned as an alignment film.

According to a fourth aspect of the present invention, an electro-optical device including the above-described liquid crystal panel is provided.

According to a fifth aspect of the present invention, a method for manufacturing a liquid crystal panel is provided. First, two substrates are provided. Next, a liquid crystal material is filled between the substrates. The liquid crystal material includes liquid crystal molecules and the above-described photosensitive monomer. Then, energy is applied to the substrate, so that the photosensitive monomers are polymerized into a polymer film on at least one of the substrates to be an alignment film.

According to a sixth aspect of the present invention, a method for manufacturing an electro-optical device including the above-described method for manufacturing the liquid crystal panel.

The present invention will become apparent from the following detailed description of the preferred but non-limiting embodiments. The following description is made with reference to the accompanying drawings.

DETAILED DESCRIPTION OF THE INVENTION

A photosensitive monomer is provided by the present invention to be applied to a method for manufacturing a liquid crystal panel. By using the photosensitive monomer, the liquid crystal molecules could be arranged well, and the manufacturing time is shortened. Also, the ability to regulate the alignment of the liquid crystal molecules is improved. The formula, the embodiment and the synthesizing method of the photosensitive monomer are illustrated first. Then, the method for manufacturing a liquid crystal panel using the photosensitive monomer is illustrated.

Photosensitive Monomer

A photosensitive monomer is provided by the present invention. The dihedral angle of the hard core structure of the photosensitive monomer is very small. The photosensitive monomer can even be an in-plane structure. Therefore, the liquid crystal molecules are arranged by the photosensitive monomer well, and the manufacturing time is shortened. After the photosensitive monomers are polymerized, the ability to regulate the alignment of the liquid crystal molecules is enhanced. The formula of the photosensitive monomer provided by the present invention is shown as follow.

n = 1~2

"$L_1$", "$L_2$", "$L_3$", "$L_4$", "$L_5$", "$L_6$" are selected from hydrogen, fluorine, chlorine, cyano (—CN), alkyl, alkylcarbonyl, alkoxycarbonyl, and alkylcarbonyloxy. Preferably, the alkylcarbonyloxy has 1 to 7 carbon atoms, in which one or more hydrogen atoms may be substituted by fluorine or chlorine.

"$R_1$", "$R_2$", "$R_3$" and "$R_4$" are selected from hydrogen, fluorine, chlorine, cyano (—CN), thiocyanato (—SCN), pentafluoro sulfanyl (—$SF_5H$), nitrite (—$NO_2$), straight-chained alkyl/branched alkyl, and a "Z-Sp-P" group. The straight-chained alkyl/branched alkyl has 1 to 12 carbon atoms, and one or two non-adjacent —$CH_2$ groups could be replaced by oxygen, sulfur, vinylene (—CH=CH—), carbonyl (C=O), caroboxyl (—COO—), carbothio (S—CO—, —CO—S), or alkyne.

Preferably, at least one of "$R_1$", "$R_2$", "$R_3$", and "$R_4$" is a "Z-Sp-P" group. More preferably, two of "$R_1$", "$R_2$", "$R_3$", and "$R_4$" are "$Z_1$-$Sp_1$-$P_1$" group and "$Z_2$-$Sp_2$-$P_2$" group and are formed symmetrically in the photosensitive monomer.

"Z" is selected from oxygen, sulfur, methyoxy (—$OCH_2$—), carbonyl (C=O), caroboxyl (—COO—), carbamoyl (—CO—$N^OR$—, $N^OR$—CO—), methylthio (—$CH_2S$—, —$SCH_2$—), ethenylcarbonyl (—CH=CH—COO—), carbonylethenyl (—COO—CH=CH—), and a single bond.

"Sp" is selected from straight-chained alkyl or branched alkyl and a single bond. The straight-chained alkyl or branched alkyl has 1 to 8 carbon atoms, and one or two non-adjacent —$CH_2$ groups could be replaced by oxygen or sulfur.

"P" is a polymerizable group. Preferably, "P" is selected from acrylate, methacrylate, vinyl, vinyloxy, propenyl ether, expoxy, group I, II, III, IV and V.

The formula of group I is shown as follow.

"U" is selected from hydrogen, methyl, fluorine, trifluoromethyl (—$CF_3$), and phenyl.

The formula of group II is shown as follow.

X is selected from hydrogen, methyl, fluorine, trifluoromethyl (—$CF_3$), and phenyl.

The group III is pyrrole-2,5-dione, and the formula of the group III is shown as follow.

The formula of group IV is shown as follow.

"Y" is selected from hydrogen, methyl, fluorine, trifluoromethyl (—$CF_3$), and phenyl.

The formula of group V is shown as follow.

"Q" is selected from hydrogen, methyl, fluorine, trifluoromethyl (—$CF_3$ ), and phenyl.

Several embodiments of the photosensitive monomer are described as follows. The formula of the photosensitive monomer is shown as follow but not limited thereto.

n=1. "$R_1$", "$R_4$", "$L_1$", "$L_2$", "$L_3$", "$L_4$", "$L_5$", "$L_6$" are hydrogen atoms. "$R_2$" and "$R_3$" are "Z-Sp-P" groups; "Z" is oxygen atom, "Sp" is ethyl, and "P" is methacrylate.

n=1. "$R_1$", "$R_4$", "$L_1$", "$L_2$", "$L_3$", "$L_4$", "$L_5$", "$L_6$" are hydrogen atoms. "$R_2$" and "$R_3$" are "Z-Sp-P" groups; "Z" is oxygen atom, "Sp" is ethyl, and "P" is the group IV in which "Y" is fluorine.

n=1. "$R_1$", "$R_4$", "$L_1$", "$L_2$", "$L_3$", "$L_4$", "$L_5$", "$L_6$" are hydrogen atoms. "R2" and "R3" are "Z-Sp-P" groups; "Z" is oxygen atom, "Sp" is ethyl, and "P" is the group IV in which "Y" is trifluoromethyl.

n=1. "$R_1$", "$R_4$", "$L_1$", "$L_2$", "$L_3$", "$L_4$", "$L_5$", "$L_6$" are hydrogen atoms. "$R_2$" and "$R_3$" are "Z-Sp-P" groups; "Z" is oxygen atom, "Sp" is ethyl, and "P" is the group IV in which "Y" is phenyl.

n=1. "R1", "R4", "L1", "L2", "L3", "L4", "L5", "L6" are hydrogen atoms. "R2" and "R3" are "Z-Sp-P" groups; "Z" is oxygen atom, "Sp" is ethyl, and "P" is the group III (pyrrole-2,5-dione).

Another embodiment will be described to illustrate the synthesizing method thereof. The photosensitive monomer, for example, is the compound 2. n=1. "$R_1$", "$R_4$", "$L_1$", "$L_2$", "$L_3$", "$L_4$", "$L_5$", "$L_6$" are hydrogen atoms. "$R_2$" and "$R_3$" are "Z-Sp-P" groups, in which "Z" and "Sp" are a single bonds and "P" is methacrylate. The chemical structure of the compound 2 is represented as formula 2. The synthesizing method and the formula are shown as follow.

-continued

2

In order to synthesize the compound 2 shown above, 2.4 g or 10 mmol of 2,6-Dihydroxyanthraquinone was dissolved in 150 ml of 2.0 N sodium carbonate ($Na_2CO_3$) solution. 4.8 g or 127 mmol of sodium borohydride ($NaBH_4$) was added into the solution slowly. The solution was stirred at room temperature for 3 hours until no gas is generated. Then, the solution was refluxed under heating and stirring for 10 minutes. After the solution was cooled down, concentrated hydrochloric acid was added to the solution for acidizing reaction. The solution was filtered to collect the residue such as sediment. The residue was dissolved by acetone, followed by drying over anhydrous magnesium sulfate ($MgSO_4$). Thereafter, the solution was filtered when vacuum is applied. Then, the filtered solution was concentrated to obtain reddish brown solid. The resulting solid was purified by column chromatography, such as silica gel column or others, using an ethyl acetate/hexane solution (such as EA/Hexane substantially equal to 1/1) as a developing solvent, and further purified by recrystallization by using ethanol. As a result, light reddish brown crystal was obtained. The light reddish brown crystal represented as the formula 1 is 2,6-Dihydroxyanthracene, which is the product of the reaction i in which the reactant is 2,6-Dihydroxyanthraquinone.

Afterwards, 2,6-Dihydroxyanthracene, obtained by the reaction i, would become a reactant in reaction ii. 0.87 g or 4.14 mmol of 2,6-Dihydroxyanthracene was added to a reactor of 250 ml (such as a two-neck bottle or others), followed by extracting air by a vacuum dehydrator/deaerator. After filling nitrogen gas in the reactor three times, a fluid adding device (such as a dropper or others) was also filled with nitrogen gas. As a result, the reaction was reacted under an anhydrous and anoxic condition. Then, 1.16 ml or 8.28 mmol of triethylamine ($Et_3N$) and 50 ml of dehydrated tetrahydrofuran (THF) were added at room temperature and stirred until dissolving. Later, 0.88 ml or 9.11 mmol of methacryloyl chloride was injected in the solution with ice bath and then was reacted at room temperature overnight. After vacuum filtered by tetrahydrofuran (THF), the filtered liquid was collected and concentrated under reduced pressure. The concentrated solution was extracted by ethyl acetate (EA) and water, followed by drying over by anhydrous magnesium sulfate ($MgSO_4$) and vacuum filtration. Afterwards, the resulting solution was concentrated with vacuum to obtain yellow solid. Thereon, the yellow solid was purified by column chromatography, such as silica gel column or the like, and then washed by a mixed solvent of ethyl acetate and hexane solution (such as EA/Hexane=1/6 by volume) to obtain light yellow solid. Later, the light yellow solid was further purified by recrystallization from a mixed solvent of THF and methanol to obtain 2,6-Dimethacryloxyanthracene (represented as formula 2).

Application of the Photosensitive Monomer

Figure 1A:
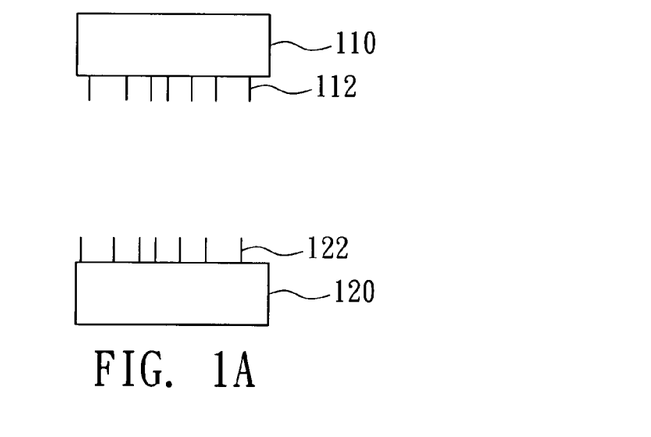
FIGS. 1A-1D illustrate a method for manufacturing a liquid crystal panel according to an embodiment of the present invention.
Figure 1B:
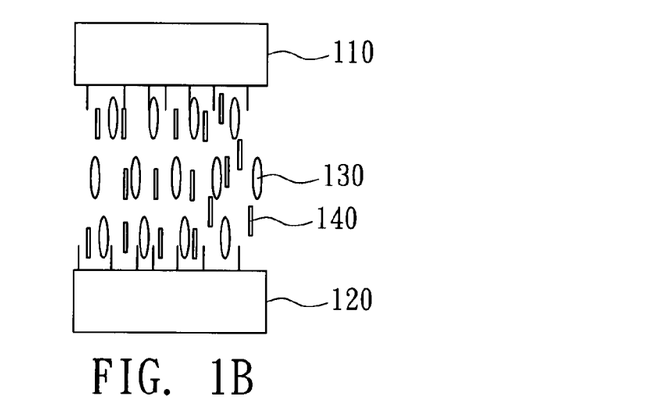
Figure 1C:
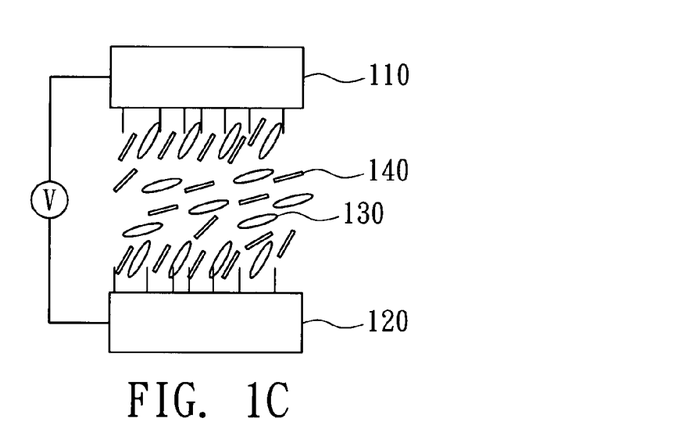
Figure 1D:
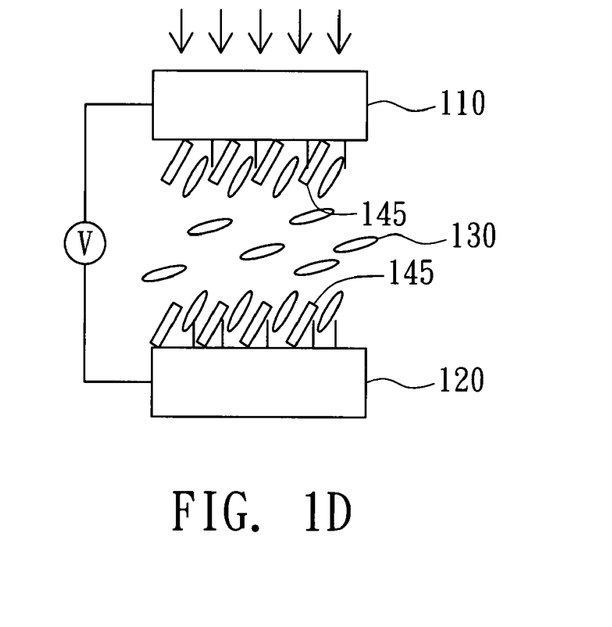

The photosensitive monomer provided by the present invention can be applied to polymer-stabilizing alignment (PSA) technology for manufacturing a liquid crystal panel. FIGS. 1A~1D illustrate a method for manufacturing a liquid crystal panel according to an embodiment of the present invention. The method for manufacturing a liquid crystal panel is described as follow. First, substrates 110 and 120 are provided, as shown in FIG. 1A. Next, a liquid crystal material is disposed between the substrates 110 and 120. The liquid crystal material includes liquid crystal molecules 130 and the photosensitive monomers 140 described above, as shown in FIG. 1B. The method for disposing the liquid crystal material includes an ODF (one-drop-fill) process or an injection process. Also, the photosensitive monomers 140 in the liquid crystal material include monomers with one or more structures mixed together. After the liquid crystal molecules and the photosensitive monomers are disposed, at least one of a heat source and a voltage is preferably applied to at least one of the substrates 110 and 120 to help at least one of the liquid crystal molecules 130 and the photosensitive monomers 140 stir well, as shown in FIG. 1C. At least one of the above-described heat source and the voltage can be applied once or several times. When at least one of the heat source and the voltage is applied several times, each time the temperature or the voltage value can be substantially the same or different. Moreover, the current type of the voltage comprises direct current, alternating current, or the combination thereof. For example, when the liquid crystal molecules 130 are driven by the voltage to rotate, the photosensitive monomers 140 rotate along with the liquid crystal molecules 130. In other words, the liquid crystal molecules 130 lead the photosensitive monomers 140 to rotate. The arrangement of the liquid crystal molecules 130 and the photosensitive monomers 140 is shown in FIG. 1C but not limited thereto. However, at least one of the heat source and the voltage is not necessarily to be applied to the substrates.

Thereon, an energy source is applied to at least one of the substrates 110 and 120, so that the photosensitive monomers 140 are polymerized to form a polymer film 145 on at least one of the substrates 110 and 120. The polymer film 145 is as an alignment film and, preferably, disposed on the substrates 110 and 120, shown in FIG. 1D, but the polymer film 145 is not limited thereto. The polymer film 145 may be disposed on one of the substrates 110 and 120. The energy source, for example, is a visible light source, an ultraviolet light source, or another light source capable of inducing the polymerization of the photosensitive monomers of the present embodiment.

Moreover, another alignment film is, preferably, formed on at least one of the substrates to enhance the alignment ability. For example, the substrate 110 includes an alignment film 112, and the substrate 120 includes an alignment film 122, as shown in FIG. 1A. Then, the above-described polymer film 145 (such as a second alignment film) is formed on the alignment film (such as a first alignment film) and is adapted to further enhance the alignment ability, but the alignment film 122 is not limited thereto. The alignment film 122 may be disposed on at least one of the substrates 110 and 120. The alignment films 112 and 122 are formed through a conventional rubbing process or a photo-alignment process.

What is worth mentioning is that the hard core structure of the photosensitive monomer 140 is an in-plane structure. When the photosensitive monomer 140 is polymerized as a polymer, the ability to regulate the alignment of the liquid crystal molecules is improved. As a result, the liquid crystal molecules in the liquid crystal panel are arranged well.

Figure 2:
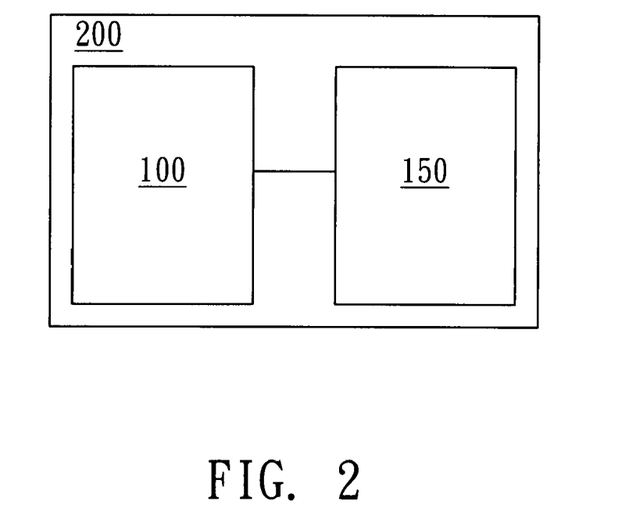
FIG. 2 illustrates an electro-optical device according the embodiment of the present invention.

Referring to FIG. 2, illustrating an electro-optical device according to the embodiment of the present invention. A liquid crystal display panel 100 according to the above-mentioned embodiment can be combined with an electronic device 150 to be an electro-optical device 200. For example, the electronic device 150 is a control device, an operation device, a processing device, an input device, a memory device, a driving device, a lighting device, a protection device, a sensor, a detecting device, or the combination thereof. The electro-optical device can be a portable product (such as a mobile phone, a camcorder, a camera, a laptop, a video game player, a watch, a music player, an email receiver/sender, a navigator, a digital frame, or a similar product), a video/audio product (such as a video/audio player or a similar product), a screen, a television, an outdoor/indoor billboard, or a panel of a projector, etc. Furthermore, the display panel of the above-mentioned embodiment of the present invention can be a transmissive, transflective, reflective, VA (vertical alignment), IPS (in-plane switching), MVA (multi-domain vertical alignment), TN (twisted nematic), STN (super twisted nematic), PVA (patterned vertical alignment), S-PVA (super patterned vertical alignment), ASV (advanced super view), FFS (fringe-field switching), CPA (continuous pinwheel alignment), ASM (axially symmetric aligned), OCB (optically compensated bend), S-IPS (super in plane switching), AS-IPS (advanced super in-plane switching), UFFS (ultra fringe-field switching), polymer stable alignment, dual-view, triple-view, or the combination thereof.

The photosensitive monomer, liquid crystal material, liquid crystal panel, method for manufacturing the same, electro-optical device and manufacturing method thereof have several advantages.

1. The alignment effect is improved. Because the hard core of the photosensitive monomer of the present embodiment is an in-plane structure, the polymer polymerized by the photosensitive monomers has great ability to regulate alignment of the liquid crystal molecules. As a result, the liquid crystal molecules in the liquid crystal panel are arranged and aligned well.

2. The light color is not deteriorated. The hard core of the photosensitive monomer has strong absorption peak between about 300 nm and about 400 nm. Because the monomer has week fluorescence or the emission wavelength is below about 400 nm, fluorescence is effectively suppressed after the reactive group is bound. In other words, the polymer film in the liquid crystal layer does not change its color or illuminates. Therefore, the liquid crystal panel or the electro-optical device using the polymer film of the embodiments of the present invention as the alignment film has good efficiency and displays colorful images.

It will be apparent to those skilled in the art that various modifications and variations can be made to the structure of the present invention without departing from the scope or spirit of the present invention. In view of the foregoing, it is intended that the present invention cover modifications and variations of this invention provided they fall within the scope of the following claims and their equivalents.

What is claimed is:

1. A photosensitive monomer of formula:

wherein n is 1 or 2;
wherein each of "$L_3$" and "$L_4$" are hydrogen,
wherein "$L_1$", "$L_2$", "$L_5$", and "$L_6$" are selected from hydrogen, fluorine, chlorine, cyano, alkyl, alkylcarbonyl, alkoxycarbonyl, and alkylcarbonyloxy having 1 to 7 carbon atoms, in which one or more hydrogen atoms are substituted by fluorine or chlorine;
wherein "$R_1$", "$R_2$", "$R_3$", and "$R_4$" are selected from hydrogen, fluorine, chlorine, cyano, thiocyanato, pentafluoro sulfanyl, nitrite, straight-chained alkyl/branched alkyl, and a "Z-Sp-P" group, straight-chained alkyl/branched alkyl having 1 to 12 carbon atoms and one or two non-adjacent 1 or 2 CH$_2$ groups are replaced by oxygen, sulfur, vinylene, carbonyl, caroboxyl, carbothio or alkyne;
wherein at least one of "$R_1$", "$R_2$", "$R_3$", and "$R_4$" is the "Z-Sp-P" group;
wherein "Z" is selected from oxygen, sulfur, methyoxy, carbonyl, caroboxyl, carbamoyl, methylthio, ethenylcarbonyl, carbonylethenyl, and a single bond;
wherein "Sp" is selected from straight-chained alkyl or branched alkyl, and a single bond, straight-chained alkyl or branched alkyl having 1 to 8 carbon atoms, and one or two non-adjacent CH$_2$ groups are replaced by oxygen or sulfur; and
wherein "P" is a polymerizable group.

2. The photosensitive monomer according to claim 1, wherein "P" is a group selected from an acrylate, a methacrylate, a vinyl, a vinyloxy, a propenyl ether, an expoxy, group I, group II, group III, group IV, and group V;
wherein group I includes formula (I):

where "U" is selected from hydrogen, methyl, fluorine, trifluoromethyl, and phenyl;
wherein group II includes formula (II):

where X is selected from hydrogen, methyl, fluorine, trifluoromethyl, and phenyl;
wherein group III includes formula (III):

wherein group IV includes formula (IV):

where "Y" is selected from hydrogen, methyl, trifluoromethyl, fluorine and, phenyl; and
wherein group V includes formula (V):

where "Q" is selected from hydrogen, methyl, fluorine, trifluoromethyl, and phenyl.

3. The photosensitive monomer according to claim 1, wherein two of "$R_1$", "$R_2$", "$R_3$" and "$R_4$" are independently the "Z-Sp-P" group and are formed symmetrically in the photosensitive monomer.

4. A liquid crystal material, comprising:
a liquid crystal molecule; and
the photosensitive monomer according to claim 1.

5. A liquid crystal panel comprising the liquid crystal material according to claim 4, wherein the photosensitive monomers are polymerized into a polymer film that is an alignment film.

6. An electro-optical device comprising the liquid crystal panel according to claim 5.

7. A method for manufacturing a liquid crystal panel, the method comprising:
a. providing two substrates;
b. disposing a liquid crystal material between the substrates, the liquid crystal material comprising a liquid crystal molecule and a photosensitive monomer, the photosensitive monomer comprising one or a plurality of compounds of formula:

wherein n is 1 or 2;
wherein each of "$L_3$" and "$L_4$" are hydrogen, and "$L_1$", "$L_2$", "$L_5$", and "$L_6$" are selected from hydrogen, fluorine, chlorine, cyano, alkyl, alkylcarbonyl, alkoxycarbonyl, and alkylcarbonyloxy having 1 to 7 carbon atoms, in which one or more hydrogen atoms are substituted by fluorine or chlorine;
wherein "$R_1$", "$R_2$", "$R_3$" and "$R_4$" are selected from hydrogen, fluorine, chlorine, cyano, thiocyanato, pentafluoro sulfanyl, nitrite, straight-chained alkyl /branched alkyl, and a "Z-Sp-P" group, straight-chained alkyl /branched alkyl having 1 to 12 carbon atoms, and one or two non-adjacent $CH_2$ groups are replaced by oxygen, sulfur, vinylene, carbonyl, caroboxyl, carbothio or alkyne;
wherein at least one of "$R_1$", "$R_2$", "$R_3$", and "$R_4$" is the "Z-Sp-P" group;
wherein "$Z_1$" is selected from oxygen, sulfur, methyoxy, carbonyl, caroboxyl, carbamoyl, methylthio, ethenylcarbonyl, carbonylethenyl, and a single bond;
wherein "Sp" is selected from straight-chained alkyl or branched alkyl and a single bond, straight-chained or branch alkyl having 1 to 8 carbon atoms, and one or two non-adjacent $CH_2$ groups are replaced by oxygen or sulfur;
wherein "P" is a polymerizable group; and
c. applying an energy source to the substrates adapted to polymerize the photosensitive monomer into a polymer film on at least one of the substrates, the polymer film as an alignment film.

8. The method according to claim 7, wherein "P" is a group selected from an acrylate, a methacrylate, a vinyl, a vinyloxy, a propenyl ether, an expoxy, group I, group II, group III, group IV and group V;

wherein group I includes formula (I)

where "U" is selected from hydrogen, methyl, fluorine, trifluoromethyl, and phenyl;

wherein group II includes formula II:

where "X" is selected hydrogen, methyl, fluorine, trifluoromethyl, and phenyl;

wherein group III includes formula (III):

wherein group IV includes formula (IV):

where "Y" is selected from hydrogen, methyl, fluorine, trifluoromethyl, and phenyl; and wherein group V includes formula (V):

where "Q" is selected from hydrogen, methyl, fluorine, trifluoromethyl, and phenyl.

9. The method according to claim 7, further comprising applying at least one of a voltage and a heat source to at least one of the substrates.

10. The method according to claim 7, wherein two of "$R_1$", "$R_2$", "$R_3$" and "$R_4$" are independently the "Z-Sp-P" group and are formed symmetrically in the photosensitive monomer.

11. The method according to claim 7, further comprising forming another alignment film on at least one of the substrates adapted to enhance the alignment effect of the alignment film formed by the photosensitive monomer.

12. A method for manufacturing an electro-optical device comprising the method for manufacturing a liquid crystal panel according to claim 7.

13. A photosensitive monomer of formula:

$$\left[ R_1 \underset{L_2}{\overset{L_1}{\diagup}} \underset{L_4}{\overset{L_3}{\diagup}} \underset{L_5}{\overset{L_5}{\diagup}} R_3 \atop R_4 \right]_n$$

wherein n is 1 or 2;

wherein "$L_1$", "$L_2$", "$L_3$", "$L_4$", "$L_5$", and "$L_6$" are selected from hydrogen, fluorine, chlorine, cyano, alkyl, alkylcarbonyl, alkoxycarbonyl, and alkylcarbonyloxy having 1 to 7 carbon atoms, in which one or more hydrogen atoms are substituted by fluorine or chlorine;

wherein "$R_1$", "$R_2$", "$R_3$", and "$R_4$" are selected from hydrogen, fluorine, chlorine, cyano, thiocyanato, pentafluoro sulfanyl, nitrite, straight-chained alkyl/branched alkyl, and a "Z-Sp-P" group, straight-chained alkyl/branched alkyl having 1 to 12 carbon atoms and one or two non-adjacent 1 or 2 $CH_2$ groups are replaced by oxygen, sulfur, vinylene, carbonyl, caroboxyl, carbothio or alkyne;

wherein at least one of "$R_1$", "$R_2$", "$R_3$", and "$R_4$" is the "Z-Sp-P" group;

wherein "Z" is selected from oxygen, sulfur, methyoxy, carbonyl, caroboxyl, carbamoyl, methylthio, ethenylcarbonyl, carbonylethenyl, and a single bond;

wherein "Sp" is selected from straight-chained alkyl or branched alkyl, and a single bond, straight-chained alkyl or branched alkyl having 1 to 8 carbon atoms, and one or two non-adjacent $CH_2$ groups are replaced by oxygen or sulfur;

wherein "P" is selected from group I, group II, group III, group IV, and group V, where group I includes formula (I):

$$\text{—N(H)—C(=O)—C(=O)—U} \quad (I)$$

where "U" is selected from fluorine and trifluoromethyl;

where group II includes formula (II):

$$\text{—N(H)—C(=O)—CH=CH—X} \quad (II)$$

where X is selected from methyl, fluorine, trifluoromethyl, and phenyl;

where group III includes formula (III):

$$\text{(maleimide group)} \quad (III)$$

where group IV includes formula (IV):

$$\text{—O—C(=O)—C(=CH_2)—Y} \quad (IV)$$

where "Y" is selected from trifluoromethyl and fluorine ; and where group V includes formula (V):

$$\text{—C(=O)—CH=CH—Q} \quad (V)$$

where "Q" is selected from methyl, fluorine, trifluoromethyl, and phenyl.

14. The photosensitive monomer according to claim 13, wherein two of "$R_1$", "$R_2$", "$R_3$" and "$R_4$" are independently the "Z-Sp-P" group and are formed symmetrically in the photosensitive monomer.

15. A liquid crystal material, comprising:
a liquid crystal molecule; and
the photosensitive monomer according to claim 13.

16. A liquid crystal panel comprising the liquid crystal material according to claim 15, wherein the photosensitive monomers are polymerized into a polymer film that is an alignment film.

17. An electro-optical device comprising the liquid crystal panel according to claim 16.

18. A method for manufacturing a liquid crystal panel, the method comprising:
 a. providing two substrates;
 b. disposing a liquid crystal material between the substrates, the liquid crystal material comprising a liquid crystal molecule and a photosensitive monomer, the photosensitive monomer comprising one or a plurality of compounds of formula:

$$\left[ R_1 \underset{L_2}{\overset{L_1}{\diagup}} \underset{L_4}{\overset{L_3}{\diagup}} \underset{L_6}{\overset{L_5}{\diagup}} R_3 \atop R_4 \right]_n$$

wherein n is 1 or 2;

wherein "L$_1$", "L$_2$", "L$_3$", "L$_4$", "L$_5$", and "L$_6$" are selected from hydrogen, fluorine, chlorine, cyano, alkyl, alkylcarbonyl, alkoxycarbonyl, and alkylcarbonyloxy having 1 to 7 carbon atoms, in which one or more hydrogen atoms are substituted by fluorine or chlorine;

wherein "R$_1$", "R$_2$", "R$_3$" and "R$_4$" are selected from hydrogen, fluorine, chlorine, cyano, thiocyanato, pentafluoro sulfanyl, nitrite, straight-chained alkyl /branched alkyl, and a "Z-Sp-P" group, straight-chained alkyl /branched alkyl having 1 to 12 carbon atoms, and one or two non-adjacent CH$_2$ groups are replaced by oxygen, sulfur, vinylene, carbonyl, caroboxyl, carbothio or alkyne;

wherein at least one of "R$_1$", "R$_2$", "R$_3$", and "R$_4$" is the "Z-Sp-P" group;

wherein "Z$_1$" is selected from oxygen, sulfur, methyoxy, carbonyl, caroboxyl, carbamoyl, methylthio, ethenylcarbonyl, carbonylethenyl, and a single bond;

wherein "Sp" is selected from straight-chained alkyl or branched alkyl and a single bond, straight-chained or branch alkyl having 1 to 8 carbon atoms, and one or two non-adjacent CH$_2$ groups are replaced by oxygen or sulfur;

wherein "P" is selected from group I, group II, group III, group IV and group V, where group I includes formula (I):

(I)

where "U" is selected from fluorine and trifluoromethyl;

where group II includes formula (II):

(II)

where "X" is selected methyl, fluorine, trifluoromethyl, and phenyl;

where group III includes formula (III):

(III)

where group IV includes formula (IV):

(IV)

where "Y" is selected from fluorine and trifluoromethyl; and where group V includes formula (V):

(V)

where "Q" is selected from methyl, fluorine, trifluoromethyl, and phenyl; and c. applying an energy source to the substrates adapted to polymerize the photosensitive monomer into a polymer film on at least one of the substrates, the polymer film as an alignment film.

19. The method according to claim 18, further comprising applying at least one of a voltage and a heat source to at least one of the substrates.

20. The method according to claim 18, wherein two of "R$_1$", "R$_2$", "R$_3$" and "R$_4$" are independently the "Z-Sp-P" group and are formed symmetrically in the photosensitive monomer.

21. The method according to claim 18, further comprising forming another alignment film on at least one of the substrates adapted to enhance the alignment effect of the alignment film formed by the photosensitive monomer.

22. A method for manufacturing an electro-optical device comprising the method for manufacturing a liquid crystal panel according to claim 18.

\* \* \* \* \*